(12) United States Patent
Dougherty

(10) Patent No.: US 6,450,006 B1
(45) Date of Patent: Sep. 17, 2002

(54) METHOD AND APPARATUS FOR CONTROL OF LINEAR ACTUATION FORCE

(76) Inventor: Steven J. Dougherty, 18310 17th St. East, Sumner, WA (US) 98390

( * ) Notice: Subject to any disclaimer, the term of this patent is extended or adjusted under 35 U.S.C. 154(b) by 0 days.

(21) Appl. No.: 09/566,208

(22) Filed: May 5, 2000

Related U.S. Application Data

(60) Provisional application No. 60/136,123, filed on May 26, 1999.

(51) Int. Cl.$^7$ ............................. G01N 7/00; G01L 23/08
(52) U.S. Cl. ........................................ 73/19.1; 73/19.01
(58) Field of Search ........................... 73/19.01, 19.03, 73/19.05, 19.06, 19.1

(56) References Cited

U.S. PATENT DOCUMENTS

| | | | |
|---|---|---|---|
| 3,911,256 A | 10/1975 | Jones | |
| 3,967,809 A | 7/1976 | Skantar | |
| 4,276,769 A | 7/1981 | Wieland et al. | |
| 4,461,165 A | 7/1984 | Kesson | |
| 4,566,311 A | 1/1986 | Barnaby | |
| 4,581,934 A | 4/1986 | Hölzl | |
| 4,700,561 A | 10/1987 | Dougherty | 73/19.05 |
| 5,243,848 A | 9/1993 | Cox et al. | 73/19.05 |
| 5,369,600 A | 11/1994 | Ito et al. | |
| 5,442,948 A | 8/1995 | Cowing | 73/19.05 |
| 5,932,792 A | 8/1999 | Dougherty | 73/19.1 |
| 6,000,629 A | 12/1999 | Tamura et al. | |
| 6,081,767 A | 6/2000 | Witt et al. | 702/55 |

Primary Examiner—Daniel S. Larkin
(74) Attorney, Agent, or Firm—Keith D. Gehr

(57) ABSTRACT

A method for the control of actuation force in apparatus for determining entrained gas-phase content of process streams wherein the apparatus comprise compression of the process stream, measurement of the compressive behavior, and calculation of the volume of the entrained gas phase. In the apparatus, a piston device is rapidly translated into the process stream. The inertia of the liquid adjacent to the end of the piston causes the volume of fluid close to the end of the piston to be compressed by the movement of the piston. A pressure sensor integrally incorporated in the end of the piston measures the pressure pulse caused by the rapid movement of the piston. The pressure pulse is inversely proportional to entrained gas phase content. An accelerometer incorporated within the piston measures the acceleration of the piston. Changes in acceleration due to factors such as actuator hysteresis and seal friction are compensated for by automatically changing power applied to the actuator device as necessary to maintain constant acceleration.

15 Claims, 8 Drawing Sheets

Section A-A

METHOD AND APPARATUS FOR CONTROL OF LINEAR ACTUATION FORCE

The present application claims priority from Provisional Application Serial No. 60/136,123, filed May 26, 1999.

This invention relates generally to the automatic control of actuation force of a rapidly linearly displaced rod or piston. While not so limited, it is particularly useful in apparatus for the determination of the entrained gas-phase content of liquids. Apparatus of this type can determine the volume of entrained gas by rapidly actuating and impacting the liquid with a piston so that the pressure increase against the piston is indicative of gas phase content

BACKGROUND OF THE INVENTION

Many test instruments and other devices make use of a rapidly accelerating force which acts against some material in order to measure a particular property. It is essential that acceleration of the device imposing the force should be consistent and reproducible. Maintaining consistent acceleration over time has proved to be a problem for various reasons. Among these can be mentioned wear of component parts or friction caused by small bits of trash being captured in seals.

Entrained gas-phase content in liquids can be measured by various direct and indirect methods. Some indirect methods include density, viscosity, and attenuation of sound waves. In general, indirect methods suffer limitations due to contributions by other factors. For example, density also depends upon general composition, and attenuation of sound waves depends upon the presence of suspended solids. Direct measurement can rely upon fluid compressibility. Simply stated, liquids are incompressible while gases are compressible. Methods relying upon fluid compressibility generally require the collection and isolation of a sample of liquid containing entrained gases. An exception to this rule is found in an earlier patent of the present inventor, U.S. Pat. No. 5,932,792. This patent describes apparatus for determining the gas content by impacting the liquid with a piston and measuring the pressure against the piston as indicative of gas content. This apparatus requires high-speed linear actuation in order to move the piston into the fluid with sufficient velocity so that the fluid adjacent to the piston, by virtue of its inertia, does not have time to move away from the end of the piston. The fluid adjacent to the end of the piston therefore serves as a dynamic containment vessel.

Actuators designed to produce linear motion experience changes in their linear translation behavior due to mechanical hysteresis and aging effects. For example, the magnetostrictive actuators described in my earlier patent utilize the change in length of a crystalline structure subjected to an external magnetic field. The migration of the microcrystalites within the crystal structure is actually not a smooth and reproducible phenomenon. Small changes in the movement pathway of the microcrystallites throughout the crystal structure result in slightly different elongation and relaxation characteristics from cycle to cycle, and over a multitude of cycles. Therefore, the actuator does not always produce the same linear translation when subjected to a given magnetic field. Other factors can influence the magnetic field itself, such as aging of the coil used to generate the magnetic field. Similar kinds of effects occur with other actuators such as piezoelectric and solenoid actuators.

In addition to changes in the linear translation characteristics of actuators, the apparatus described in my earlier patents is affected over time by other factors, such as seal friction, that can hinder piston movement to greater or lesser degrees over time.

Therefore, because a constant applied motivational force to an actuator incorporated within my earlier apparatus may not provide an identical linear displacement characteristic of the impacting piston from cycle to cycle, the pressure measured at the end of the impacting piston, at an otherwise constant entrained gas content, may drift over time.

The present invention describes a method for overcoming this problem. However, it is more broadly useful for automatic control of the intensity and acceleration of the pulsed rapid linear movement of any similar device.

SUMMARY OF THE INVENTION

I have now discovered that in an apparatus of the type described in my earlier patent, the magnitude of the pressure pulses correlate closely with the acceleration of the impacting piston at a constant entrained gas content. Therefore, independent control of the acceleration of the impacting piston will ensure that reproducible pressure pulses are obtained at a given constant entrained gas content. The acceleration can be measured directly with an accelerometer. Alternatively, the acceleration can be calculated from the change in linear displacement over time since the second derivative of displacement with respect to time is identical to acceleration.

The acceleration produced during an actuator cycle could be expected to proceed as follows. Initially, when the actuator is at idle, there is zero acceleration. When the actuator begins to move the impacting piston into the fluid there is an increase in acceleration. When the linear movement of the impacting piston begins to decrease to zero, the acceleration decreases and approaches zero. As the impacting piston is retracted, the acceleration is negative. Finally, when the impacting piston has again come to rest, the acceleration becomes zero. As has been observed in actual practice, the characteristics of the acceleration are much more complicated than given by the preceding description. The acceleration may actually go through several positive peaks before the acceleration becomes negative. The complex behavior in the acceleration of the impacting piston results in a multiplicity of pressure responses at the end of the impacting piston.

The acceleration which occurs early in an impact cycle has the most important influence on the resulting pressure pulses even though subsequent acceleration may be greater than the early acceleration. Whereas the inertia of the fluid adjacent to the end of the piston causes the fluid to serve as a dynamic containment vessel, this effect will diminish rapidly as the fluid does begin to move under the action of the piston. Therefore, the first pressure pulse is most indicative of entrained gas content, while subsequent pressure pulses reflect a combination of compression of the fluid and simple inertial acceleration of the bulk fluid. Emphasis is therefore placed on the measurement of the early acceleration for the purpose of controlling the ability of the impacting piston to measure the entrained gas content.

The preferred method to measure the acceleration is with a dedicated accelerometer. Alternatively, a linear displacement transducer can be used to measure the position of the impacting piston over time, and acceleration can be calculated from the shape of the displacement-time curve.

A principal object of the present invention is to provide a method and apparatus for the automatic control of the amount of activation energy applied to a linear actuator so that the resultant acceleration will exhibit minimal drift over time.

Another object is to provide a method and apparatus for automatic control of activation energy applied to a rapidly translating piston used to measure entrained gas within a liquid.

A further object is to combine multiple acceleration responses in order to produce a single representative value of acceleration for control of energy applied to the actuator.

It is an additional object of the invention to provide a method and apparatus to control the performance of an actuator by measuring the acceleration of an impacting piston, and to use that information to automatically control the actuator as necessary to maintain constant acceleration.

These and many other objects will become readily apparent upon reading the following detailed description, taken in conjunction with the drawings.

DESCRIPTION OF THE PREFERRED EMBODIMENTS

Various products of specific manufacturers found to be satisfactory in my apparatus will be noted in the following description. However, it is not my intent to endorse these particular products over similar ones from other suppliers that would be equally suitable.

Figure 1:
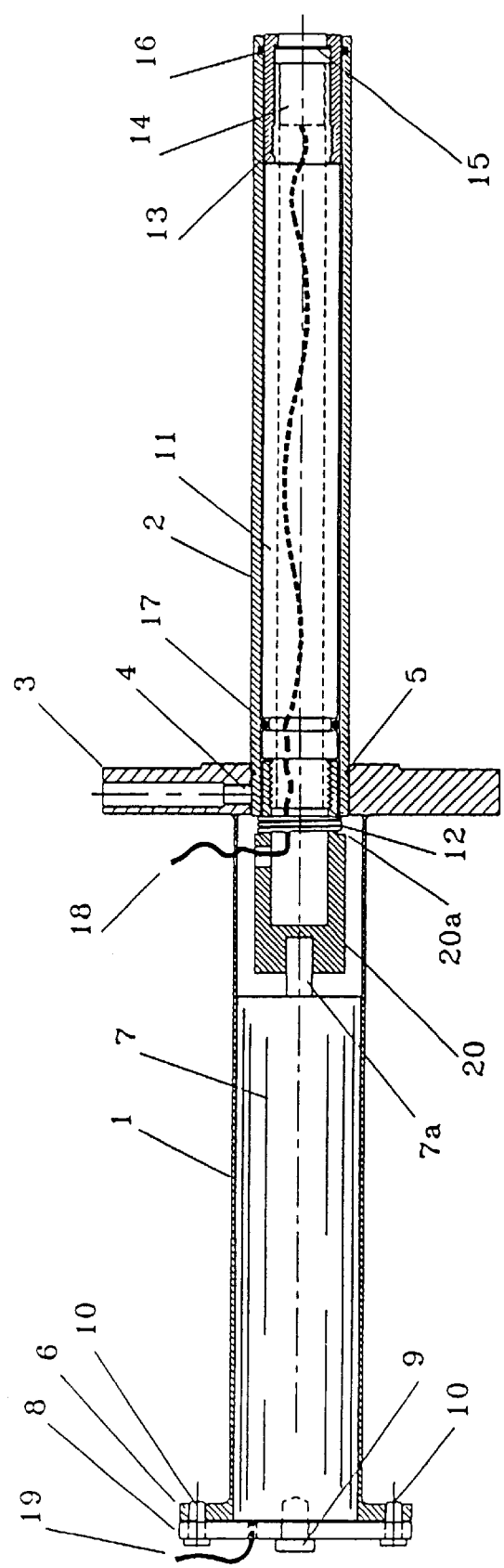
FIG. 1 is an open cross section of the apparatus, excluding any transducers for position and acceleration measurement of the impacting piston.
Figure 2:
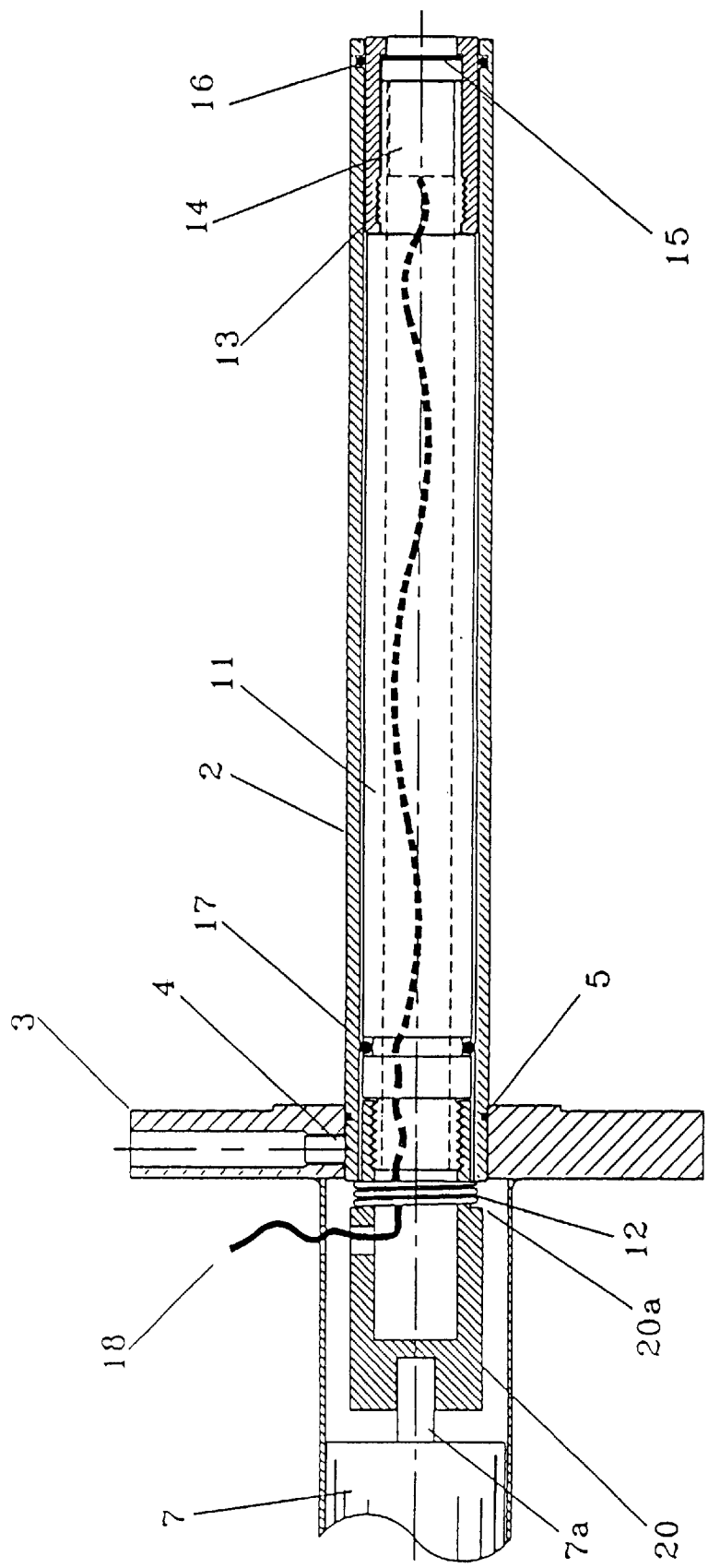
FIG. 2 is an open cross section of the apparatus shown in FIG. 1, showing selected detail.

Referring to FIGS. 1 and 2, an embodiment of the apparatus is constructed as follows. Actuator housing 1, connecting rod housing 2, and mounting flange 3 provide the framework for the apparatus. Actuator housing 1 is secured to mounting flange 3; e.g., by welding or threading. Connecting rod housing 2 slips into mounting flange 3, and is locked in place with set screw 4. O-ring 5 provides a seal. Actuator housing top flange 6 is welded to actuator housing 1. In a preferred version of the apparatus, actuator 7 is any suitable actuator means capable of producing a linear actuation of about 0.013 mm (0.005 in) over a time of about 400 microseconds. In the preferred embodiment, actuator 7 is a magnetostrictive actuator. One actuator found satisfactory is Model No. AA140J025 made by Etrema Products, Inc., Ames, Iowa. Actuator 7 is attached to top cover 8 by means of bolt 9. Top cover 8 is attached to actuator housing top flange 6 with bolts 10. Connecting rod housing 2 and mounting flange 3 provide a means for inserting the apparatus into a process stream. Connecting rod housing 2 may have a diameter of about 38 mm (1½ in) and a length of about 250 mm (10 in). Connecting rod adapter 20 is threaded to connecting rod 11. The assembly of connecting rod adapter 20 along with connecting rod 11 acts as a piston and contacts actuator rod 7a. Connecting rod adapter 20 has a proximal end held against actuator rod 7a by a biasing means 12 which may be any suitable elastic device such as a spring or an O-ring. The biasing means 12 is held between the shoulder end 20a of connecting rod adapter 20 and the end of the connecting rod housing 2.

Pressure transducer housing 13 is threaded to connecting rod 11. Pressure transducer 14 is inserted into the distal end of connecting rod 11 and held in place by pressure transducer housing 13. Pressure transducer 14 is of flush diaphragm construction, and utilizes any common methods for the sensing of pressure, including strain, piezoelectricity, and capacitance. A suitable transducer is Model No. AB100PSIS, manufactured by Data Instruments, Acton, Me.

The combination of the connecting rod adapter 20, the connecting rod 11, the pressure transducer housing 13, and the pressure transducer 14 is called the "impacting piston" in the following discussion and description.

O-ring 15 provides a seal between pressure transducer housing 13 and pressure transducer 14. O-ring 16 provides a seal between the pressure transducer housing 13 and the connector rod housing 2. O-ring 16, in addition to serving as a seal, acts with O-ring 17 to serve as bearings between the stationary connector rod housing 2 and the moveable assembly comprised of connecting rod adapter 20, connecting rod 11, and pressure transducer housing 13. The grooves for O-rings 16 and 17, measured in the axial direction, are wider than the O-ring diameters, thereby allowing the O-rings 16 and 17 to roll and deform elastically as the assembly comprised of connecting rod adapter 20, connecting rod 11, and pressure transducer housing 13 is translated in the axial direction by means of actuator 7. Pigtails 18 and 19 provide for connection to the electronics processors.

Figure 3:
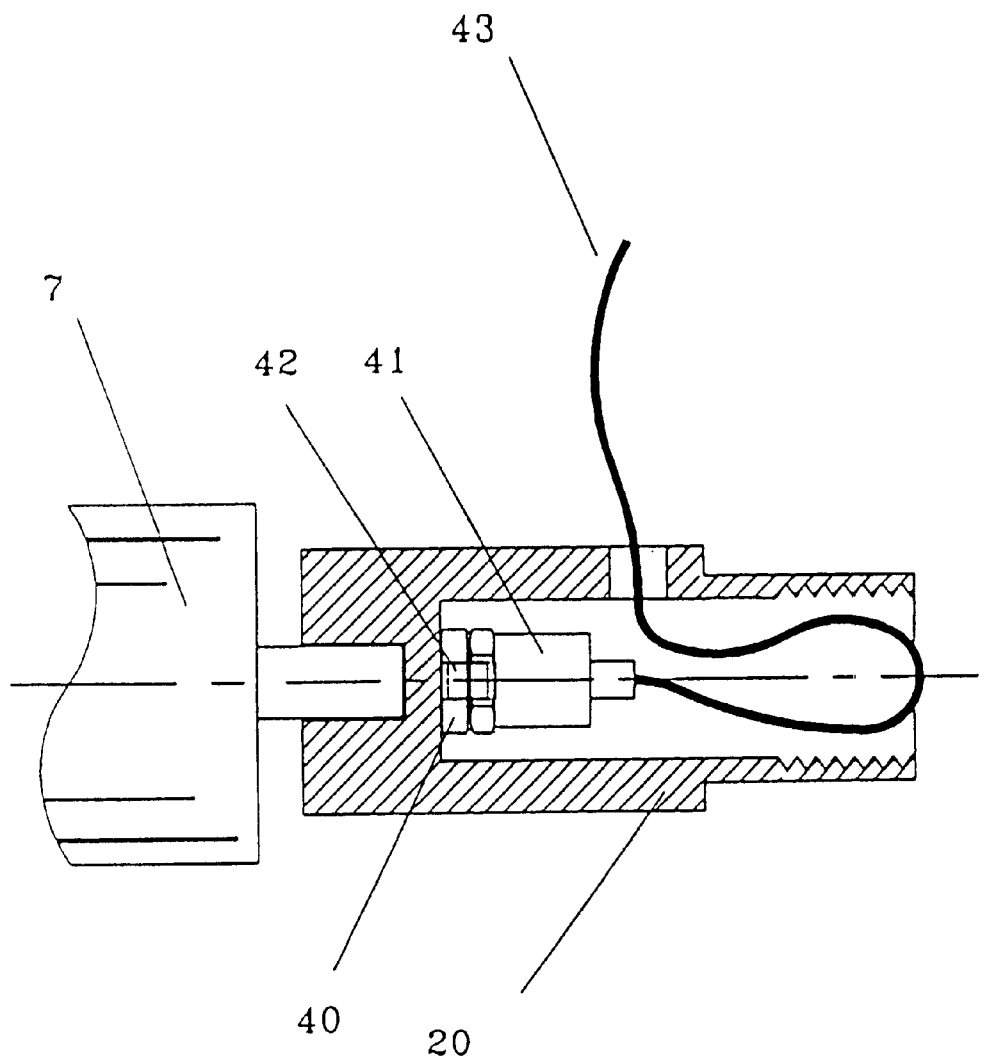
FIG. 3 is a drawing of one possible accelerometer installed within the apparatus of FIG. 1.

FIG. 3 illustrates a modified apparatus that uses an accelerometer to measure the acceleration characteristics of the impacting piston. Accelerometer 41 is attached to base plate 40 by means of a threaded stud 42. Base plate 40 is attached to connecting rod adapter 20 by means of a suitable adhesive, such as an epoxy. Base plate 42 is electrically insulating and serves primarily to electrically isolate accelerometer 41 from the apparatus. When actuator 7 is activated, the increase in actuator length causes connecting rod adapter 20 to move axially away from the actuator. The resultant acceleration is measured by accelerometer 41. The resultant electrical response is carried by wires 43 to the electronics processor. A suitable accelerometer is Model 8704B, manufactured by Kistler Instrumentation Corp., Amherst, N.Y.

Figures 4, 4A:
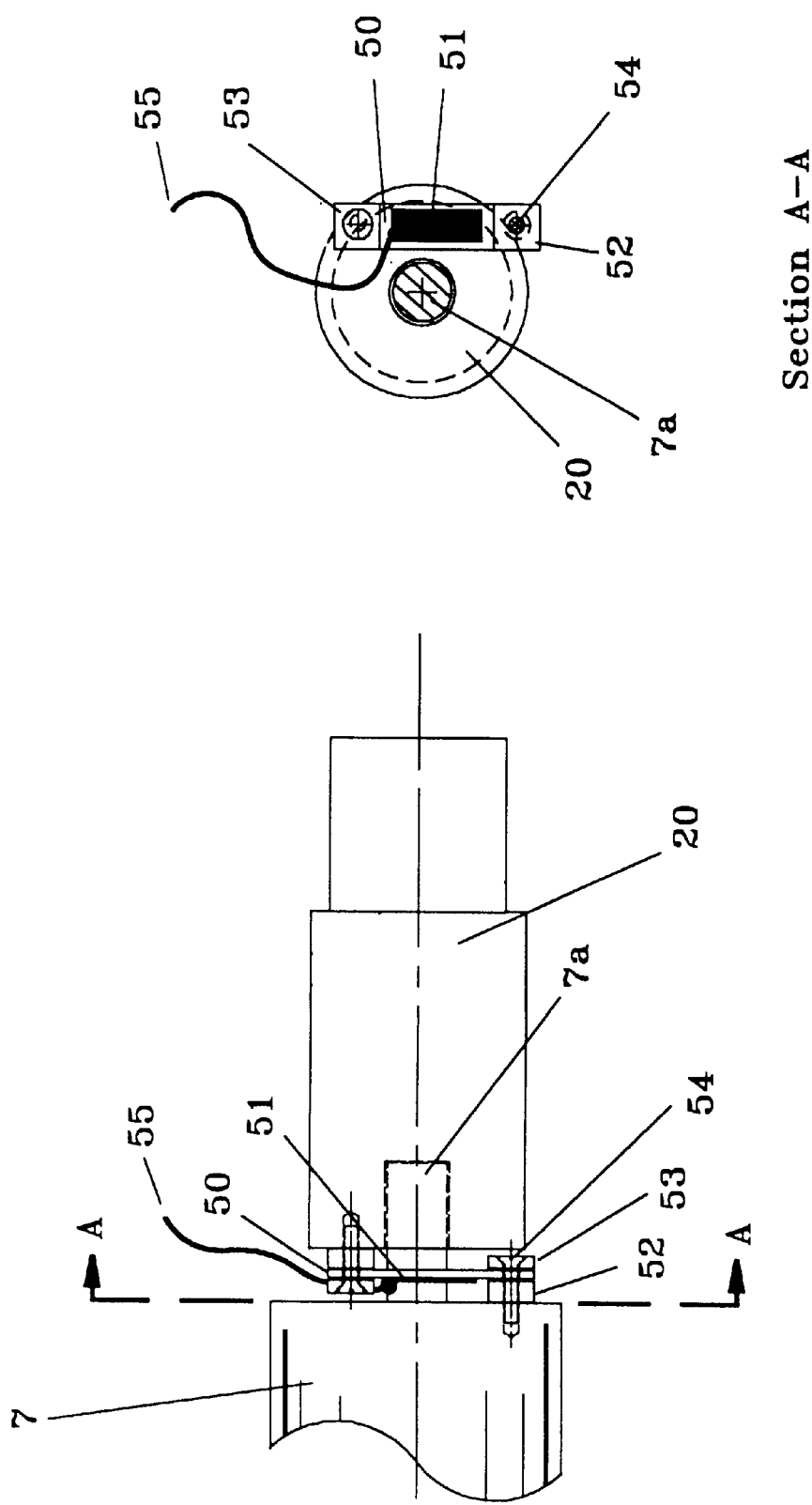
FIG. 4 is a drawing of one possible linear displacement sensor installed within the apparatus of FIG. 1.
FIG. 4A represents a section along line A—A of FIG. 4.

FIGS. 4 and 4A illustrate a modified apparatus which utilizes a strain gauge as a linear displacement transducer. Resistive strain elements 51 are bonded to flexible substrate 50. Flexible substrate 50 is rigidly clamped at each end between blocks 52 and 53. Attachment screws 54 rigidly attach the clamped flexible substrate 50 to actuator 7 on one end, and to connecting rod adapter 20 at the other end. When actuator 7 is activated, the increase in actuator length causes connecting rod adapter 20 to move axially away from the actuator 7, which in turn causes the flexible substrate 50 and the bonded strain elements 51 to be deformed. The resistive strain elements 51 are typically oriented in a Wheatstone bridge arrangement. The deformation of the strain elements 51 causes a change in voltage across the Wheatstone bridge. The voltage change, which is proportional to linear displacement, is carried by wires 55 to the electronics processor. A preferred combination of resistive strain elements 51 and flexible substrate 50 is Model FR1020D, manufactured by Futek, Irvine, Calif. It is readily apparent that alternative means can be devised to attach other linear displacement transducers, such as linearly variable displacement transformers (LVDT), or optical gauging devices.

Figure 5:
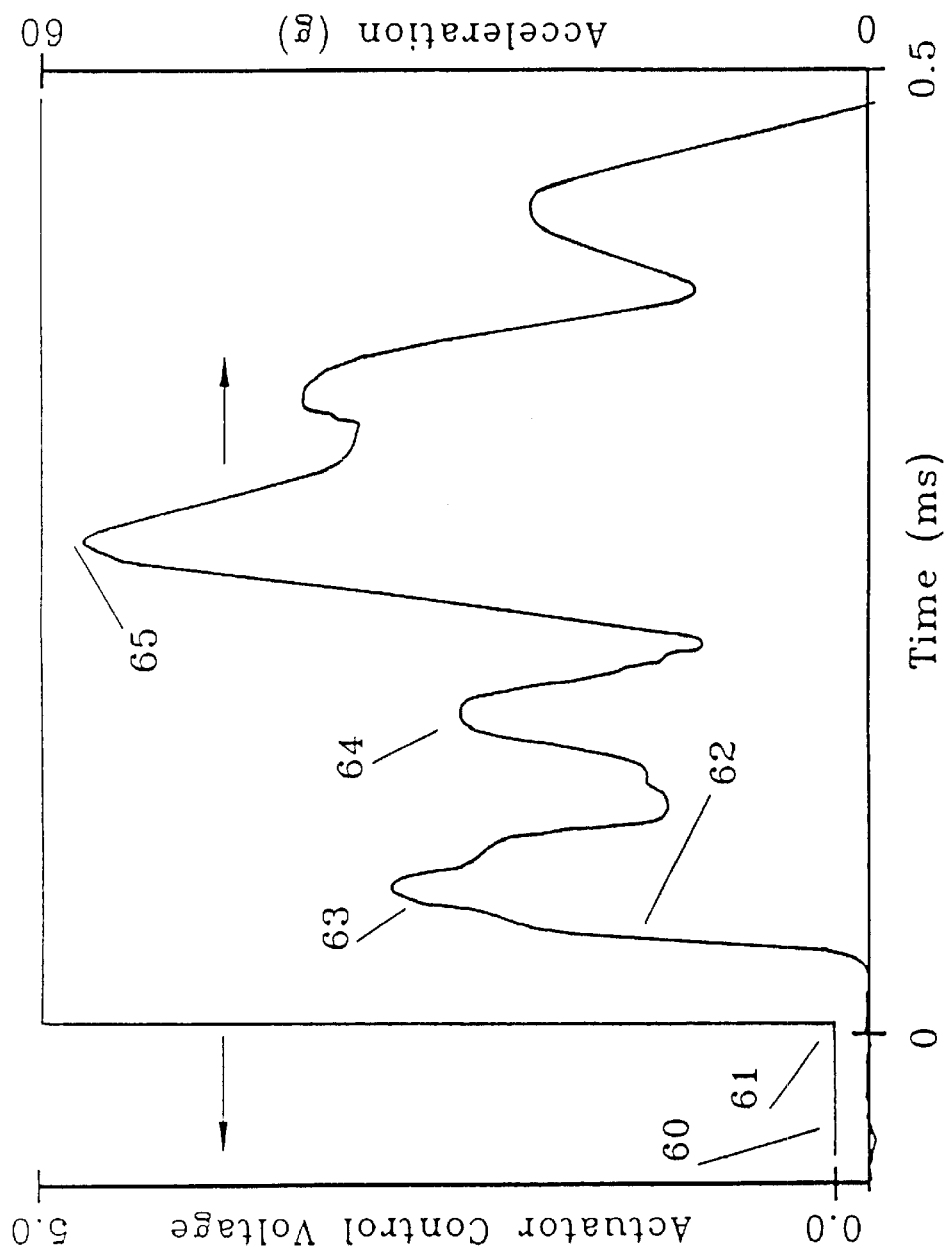
FIG. 5 is a graphical representation of an oscilloscope trace representing typical acceleration responses during an actuation cycle.

FIG. 5 illustrates an oscilloscope trace of a typical acceleration response during an actuation cycle. Actuator control voltage 60 is a low level voltage signal that controls the application of power to actuator 7 (FIG. 1). When actuator control voltage 60 drives high, as indicated at position 61, power is applied to actuator 7. Acceleration curve 62 depicts the acceleration response to the resultant actuator 7 movement.

The acceleration curve 62 increases through several distinct peaks. For the particular activation energy being provided to the actuator 7, the amplitude of the first three peaks (shown at 63, 64, and 65) are approximately 37, 32, and 60 g, at times of 70, 160, and 270 microseconds, respectively. In a preferred embodiment, a weighted sum of the first three peaks has been found to provide sufficient information for satisfactory control of the activation energy to be applied to the actuator 7. Although the area under the acceleration vs. time curve also provides information suitable for control of the activation energy, I have discovered that the effect of acceleration on the measured pressure pulses diminishes during the actuation time. Thus, selective combination of the acceleration peaks provides the most useful information.

The particular acceleration response depicted in FIG. 5 is not a singular response. That is, with different applied activation energies, the number of peaks, the peak amplitudes, and the times observed for the acceleration peaks may change significantly.

The acceleration has been found to be entirely independent of the entrained gas content in the liquid. This result is to be expected since the resistance to motion of the impacting piston is much more dependent upon the inertia of the impacting piston, the friction of the seals 16 and 17, and the resistance of the biasing means 12 (FIG. 1), than it is to the inertia of the liquid adjacent to the end of the impacting piston.

Figure 6:
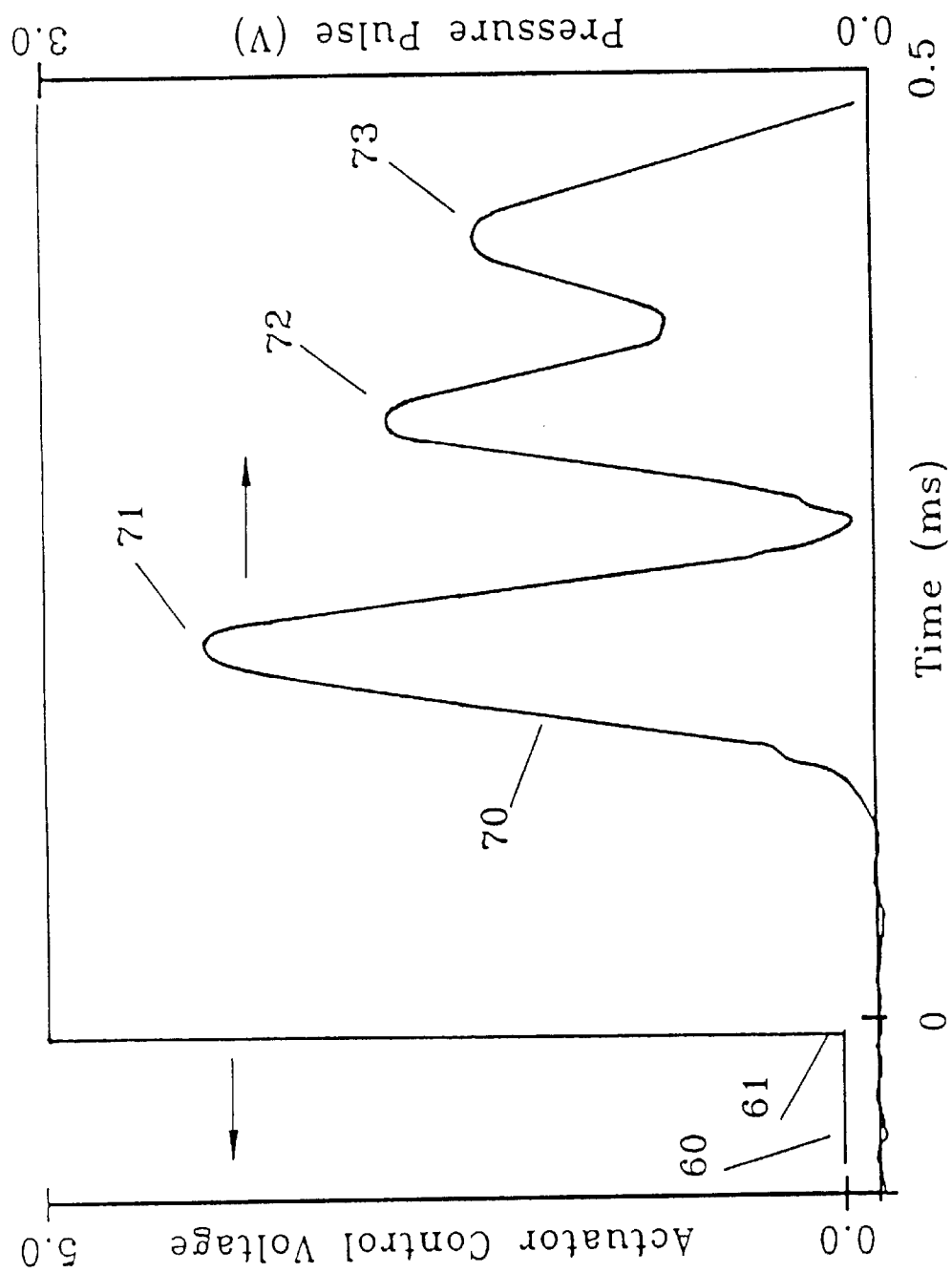
FIG. 6 is a graphical representation of an oscilloscope trace showing typical pressure pulse responses during an actuation cycle.

FIG. 6 illustrates an oscilloscope trace of a typical pressure pulse response during an actuation cycle. The actuator operating conditions were identical to those used to generate the acceleration results shown in FIG. 5. Actuator control voltage 60 is a low-level voltage signal that controls the application of power to actuator 7 (FIG. 1). When actuator control voltage 60 drives high, as indicated at position 61, power is applied to actuator 7. Pressure pulse curve 70 depicts the pressure response to the resultant actuator 7 movement.

The entrained gas content was zero for the particular pressure pulse results depicted in FIG. 6. The first pressure pulse 71 has been found to be highly sensitive to low entrained gas contents, below 5–10% by volume. The second and third pressure pulses 72 and 73 are relatively insensitive to entrained gas contents below 1–2% by volume. In a preferred embodiment, the first pressure pulse 71 is selected for low entrained gas contents, while the second and third pulses 72 and 73 are selected for measurements at higher entrained gas contents.

Figure 7:
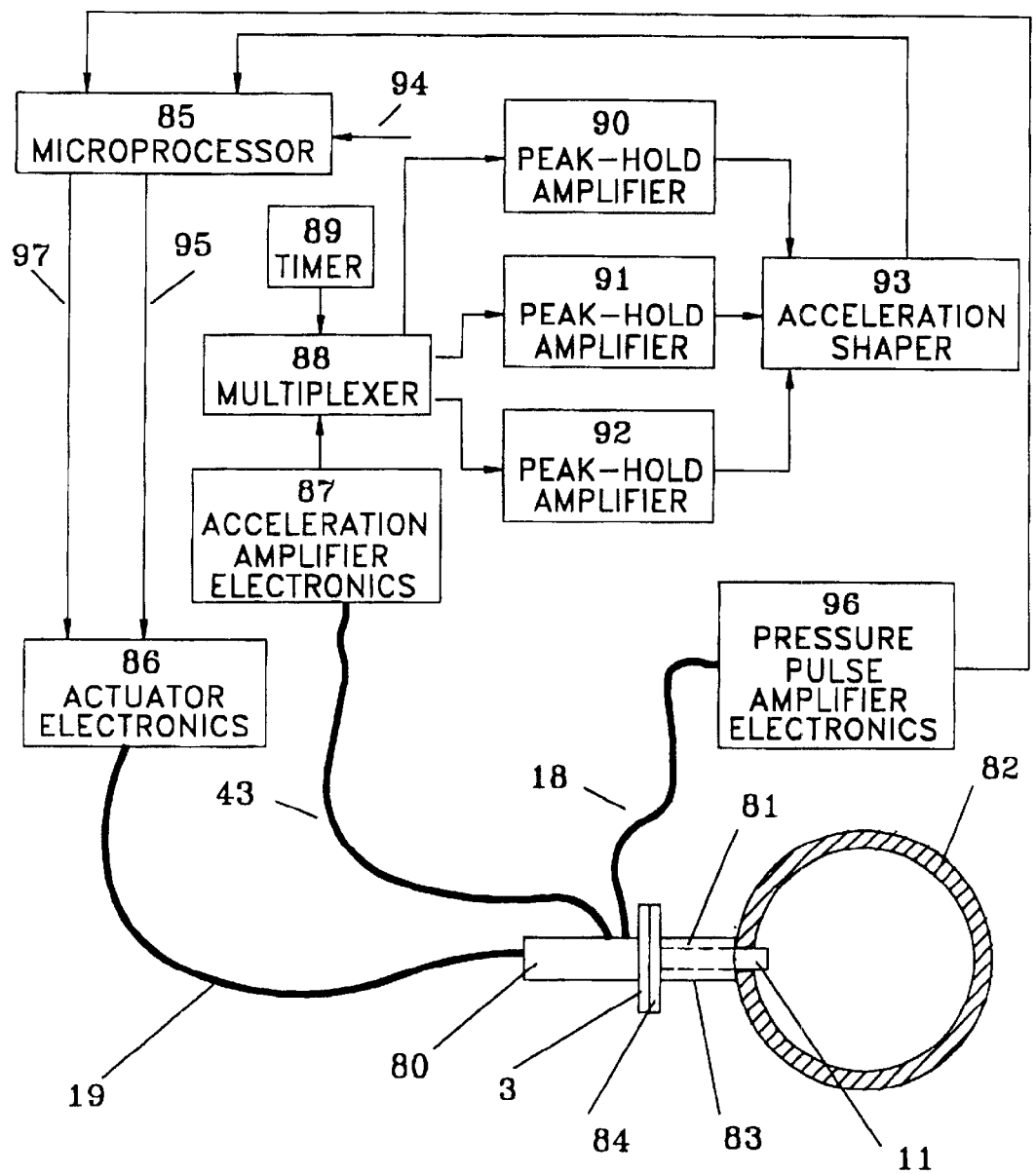
FIG. 7 is a schematic diagram of a system providing closed-loop control of the actuator power to maintain constant acceleration of the impacting piston.

Referring to FIG. 7, a system for providing an acceleration controlled impacting piston and a measurement of entrained gas content suitable for process control is explained as follows. Apparatus 80, previously described in FIGS. 1–4, is inserted through assembly 81 into process pipe 82, containing the process fluid. Assembly 81 consists of pipe nipple 83 and flange 84. Pipe nipple 83 may be welded to process pipe 82. Flange 84 may be welded or threaded to pipe nipple 83. Flange 84 on assembly 81, and flange 3 on assembly 80, are bolted together to complete the insertion of assembly 80 into process pipe 82. Pipe nipple 83 is of suitable length so that the distal end of connecting rod 11 protrudes into process pipe 82.

Microprocessor 85 passes a signal 97 (trace 60–61 in FIGS. 5 and 6) on a regular interval to actuator electronics 86. Actuator electronics 86 then passes a voltage pulse to activate actuator 7 (FIG. 1) in apparatus 80 through pigtail 19. The resulting pressure-pulse electrical signal is passed through pigtail 18 to pressure pulse amplifier electronics 96.

Pressure pulse amplifier electronics 96 amplifies and conditions the pressure pulse electrical signal and combines the desired pressure pulse peak characteristics (peaks 71–73 in FIG. 6) as appropriate for process requirements. The conditioned pressure pulse signal is read by microprocessor 85. Microprocessor 85 converts the pressure pulse signal to the equivalent entrained gas content by means of a calibration table, and the result is transmitted in digital and/or analog forms suitable for use in process control.

The acceleration electrical signal is passed through wires 43 to acceleration amplifier electronics 87. Acceleration amplifier electronics 87 amplifies and conditions the acceleration electrical signal. As directed by timer 89, multiplexer 88 passes the conditioned accelerometer electrical signal to peak-hold amplifiers 90, 91, and 92. Three peak-hold amplifiers are depicted in FIG. 7. The actual number of amplifiers can be greater or smaller, depending upon processing requirements. The peak hold amplifiers 90, 91, 92, along with the accelerometer signal routing effected with the timer 89 and multiplexer 88, allows the individual accelerometer peaks, such as peaks 63, 64, and 65 in FIG. 5 to be captured and held. The captured and held peaks are passed to acceleration shaper 93. Acceleration shaper 93 performs a weighted addition of the captured and held peaks. For example, with the apparatus of the preferred em-as described in FIGS. 1, 2, and 3, an optimal combination is to fully weight peaks 63 and 65, while adding only half of the magnitude of peak 64. In practice, peak 64 contributes relatively less useful information for closed-loop control of the acceleration. The shaped acceleration result is passed to microprocessor 85. The desired acceleration setpoint 94 is provided to the microprocessor 85 as a separate signal. Acceleration setpoint 94 may be conveniently produced by an external adjustable potentiometer. Microprocessor 85 compares the difference between the desired acceleration as provided by the acceleration setpoint 94 with the actual acceleration and, using standard control algorithms, calculates and passes an adjusted control signal 95 to actuator electronics 86. Actuator electronics 86 produces an appropriately modified voltage pulse to actuator 7 upon the next actuation cycle.

Figure 8:
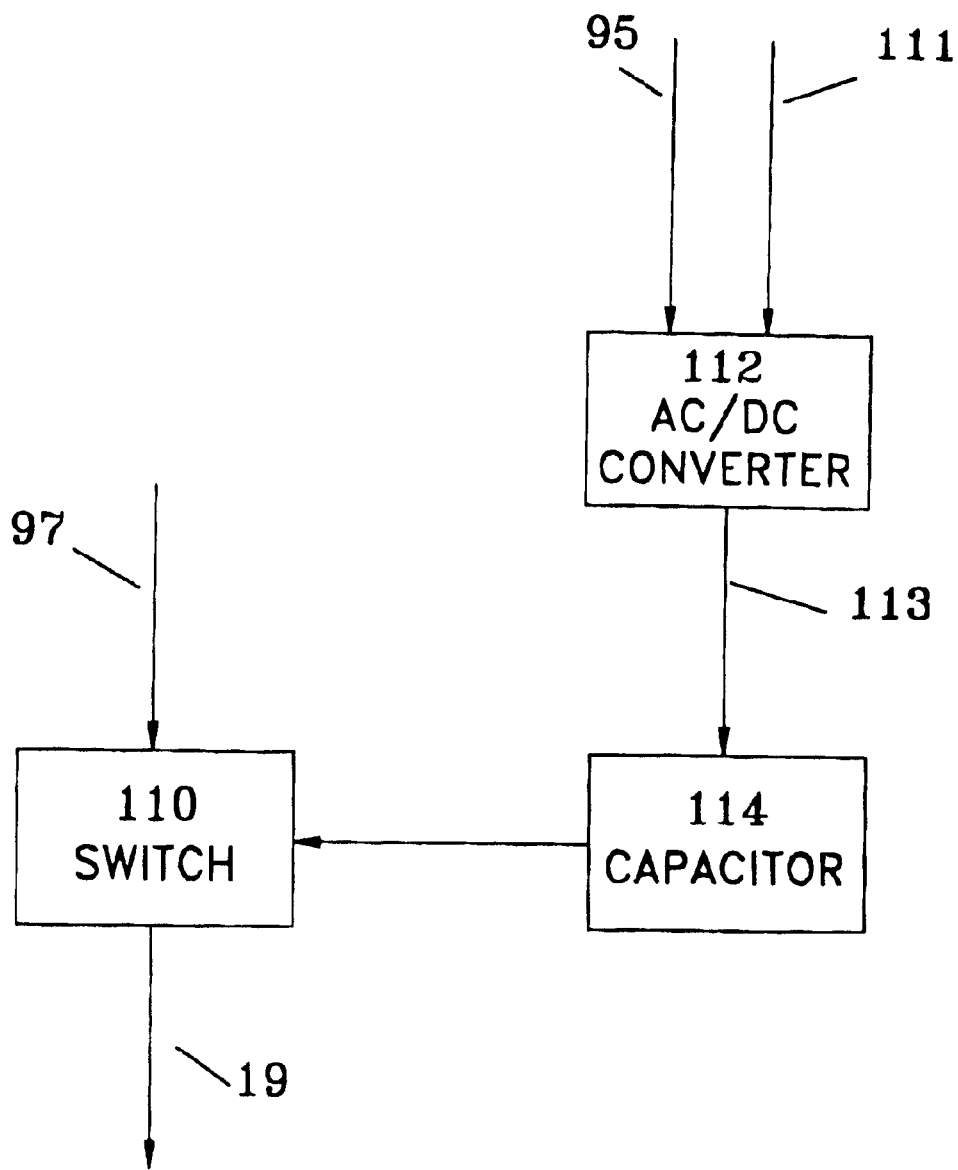
FIG. 8 is a schematic diagram of a system for providing power to an actuator during an actuation cycle.

FIG. 8 illustrates further detail of a suitable actuator electronics means 86 (FIG. 7) for providing controlled power to the actuator 7. AC voltage 111 is provided to AC to DC converter 112 to produce DC voltage 113. Signal 95 provided from microprocessor 85 (FIG. 7) controls the magnitude of the DC power from the AC to DC converter 112. In the preferred embodiment, DC voltage 113 is controlled between, for example, 50 to 250 volts, as the control signal 95 is varied between, for example, 1 to 5 volts. A suitable AC to DC converter 112 is model 1/4 A12, manufactured by Ultravolt Corp., Ronkonkoma N.Y. DC voltage 113 is stored by capacitor 114. Upon command from signal 97, switch 110 passes the stored DC voltage from capacitor 114 through wires 19 to actuator 7 (FIG. 1). In the preferred embodiment, switch 110 is a commonly available mosfet (solid state switch). The electrical current available from AC to DC converter 112 is low, for example, 10 ma, whereas the current draw by actuator 7 is high, for example, 4–8 amperes. The correspondingly rapid discharge of power from capacitor 114 results in a brief application to actuator 7 of a voltage pulse which is an order of magnitude or more above the normal voltage limit of actuator 7. Therefore, actuator 7 produces an acceleration an order of magnitude or greater than could otherwise be obtained.

It will be readily apparent to those skilled in the art that many minor variations in the invention can be made that have not been described herein. It is the intent of the inventor that these variations should be included within the scope of the invention if encompassed within the following claims.

What is claimed is:

1. Apparatus for automatic control of the activation energy applied to a linear actuator which comprises:

an actuator and an axially extending output connecting rod coupled at its proximal end to the actuator;

activating means for causing the actuator to deliver a cyclic pulsed rapid movement to the connecting rod;

acceleration sensing means coupled to the connecting rod to measure acceleration during each cycle; and a control unit receiving acceleration values and providing feedback to control energy applied to the actuator in order to correct any drift and ensure an essentially constant preset acceleration of the connecting rod from cycle to cycle.

2. The apparatus of claim 1 in which the acceleration sensing means is an accelerometer.

3. The apparatus of claim 1 in which the acceleration sensing means is a linear displacement transducer in association with electronic circuitry to convert displacement over time to acceleration and provide feedback to and control of the activating means.

4. The apparatus of claim 3 in which the linear displacement transducer is a strain gauge.

5. The apparatus of claim 1 in which the control unit combines multiple acceleration responses to produce a single representative value of acceleration.

6. The apparatus of claim 1 further including a pressure transducer means located at the distal end of the connecting rod.

7. The apparatus of claim 6 further including mounting means for the apparatus adapted so that the pressure transducer may be located within a liquid process stream whereby gas bearing liquid in the locus of the transducer would be compressed during the initial phase of the actuation cycle, the degree of compression being sensed by the transducer and directly related to the amount of entrained gas in the liquid.

8. Apparatus for measuring entrained gas in a liquid which comprises:

a housing containing an actuator and a piston-like connecting rod, the connecting rod being operatively coupled at its proximal end to the actuator and extending axially from the actuator;

a pressure transducer means located at the distal end of the connecting rod;

mounting means for the apparatus adapted so that the pressure transducer may be located within a liquid process stream;

activating means for causing the actuator to deliver a cyclic pulsed rapid movement of low linear amplitude to the connecting rod and pressure transducer; and acceleration sensor means coupled to the connecting rod and providing input to control means to ensure an essentially constant preset acceleration of the connecting rod from cycle to cycle whereby gas bearing liquid in the locus of the pressure transducer would be compressed during the initial phase of the cycle, the degree of compression being sensed by the transducer and directly related to the amount of entrained gas.

9. The apparatus of claim 8 in which the acceleration sensing means is an accelerometer.

10. The apparatus of claim 9 further in association with electronic circuitry providing feedback to and control of the activating means.

11. The apparatus of claim 8 in which the acceleration control means is a linear displacement transducer in association with electronic circuitry to convert displacement over time to acceleration and provide feedback to and control of the activating means.

12. The apparatus of claim 11 in which the linear displacement transducer is a strain gauge.

13. A method of controlling apparatus for measuring entrained gas in a liquid which comprises:

providing a housing containing an actuator and a piston-like connecting rod, the connecting rod being operatively coupled at its proximal end to the actuator and extending axially from the actuator;

locating a pressure transducer means at the distal end of the connecting rod;

mounting the apparatus so that the pressure transducer is located within a liquid process stream;

pulsing the actuator to deliver a cyclic rapid movement of low linear amplitude to the connecting rod and pressure transducer; and sensing acceleration of the connecting rod during delivery of a pulse and providing feedback to the actuator to control acceleration and ensure an essentially constant preset acceleration of the connecting rod from cycle to cycle whereby gas bearing liquid in the locus of the transducer is compressed during the initial phase of the cycle, the degree of compression being sensed by the transducer and directly related to the amount of entrained gas.

14. The method of claim 13 which includes sensing acceleration by an accelerometer operatively associated with the connecting rod.

15. The method of claim 13 which includes sensing acceleration by means of a linear displacement transducer measuring connecting rod travel over time and converting the measurement to acceleration.

* * * * *